United States Patent [19]
Henrickson et al.

[11] Patent Number: 6,015,664
[45] Date of Patent: *Jan. 18, 2000

[54] MULTIPLEX PCR ASSAY USING UNEQUAL PRIMER CONCENTRATIONS TO DETECT HPIV 1,2,3 AND RSV A,B AND INFLUENZA VIRUS A, B

[75] Inventors: Kelly J. Henrickson, Oconomowoc; Jiang Fan, Wauwatosa, both of Wis.

[73] Assignee: MCW Research Foundation, Milwaukee, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/691,045

[22] Filed: Aug. 1, 1996

Related U.S. Application Data

[63] Continuation-in-part of application No. 08/552,907, Nov. 3, 1995, Pat. No. 5,744,299.

[51] Int. Cl.[7] ............................. C12Q 1/68; C12Q 1/70; C12P 19/34; C07H 21/04
[52] U.S. Cl. ............................. 435/5; 435/6; 435/91.1; 435/91.2; 536/23.1; 536/24.3; 536/24.32; 536/24.33
[58] Field of Search .................. 435/6, 5, 91.2, 435/91.1; 536/23.1, 24.3, 24.32, 24.33, 25.3

[56] References Cited

U.S. PATENT DOCUMENTS

| | | | |
|---|---|---|---|
| 5,176,995 | 1/1993 | Sninsky et al. | 435/6 |
| 5,288,630 | 2/1994 | Wathen . | |
| 5,508,168 | 4/1996 | Orle et al. . | |
| 5,518,900 | 5/1996 | Nikiforov et al. | 435/91.1 |
| 5,744,299 | 4/1998 | Henrickson et al. | 435/5 |
| 5,882,856 | 3/1999 | Shuber | 435/6 |

FOREIGN PATENT DOCUMENTS

| | | | |
|---|---|---|---|
| 418960A3 | 3/1991 | European Pat. Off. | C12Q 1/68 |

OTHER PUBLICATIONS

Henrickson, et al., "Antibody response in children to antigen sites on human PIV–3 HN: correlation with known epitopes mapped by monoclonal antibodies," *Vaccine* 8:75–80 (1990).

Henrickson, et al., "Neutralizing epitopes of human parainfluenza virus type 3 are conformational and cannot be imitated by synthetic peptides," *Vaccine* 9:243–249 (1991).

Henrickson, K.J., "Monoclonal Antibodies to Human Parainfluenza Virus Type 1 Detect Major Antigenic Changes in Clinical Isolates," *J. Infect. Dis.* 164:1128–1134 (1991).

Henrickson, et al., "Genetic Variation and Evolution of Human Parainfluenza Virus Type 1 Hemagglutinin Neuraminidase: Analysis of 12 Clinical Isolates," *J. Infect. Dis.* 166(5) :995–1005 (1992).

Henrickson, K.J., Human Parainfluenza Viruses. In, E.H. Lennette (ed.), *Diagnostic Procedures for Viral, Rickettsial and Chlamydial Infections.* American Public Health Association (1993).

Henrickson, et al., "Epidemiology and cost of human parainfluenza virus types 1 and 2 infection in young children," *Clin. Infect. Dis.* 18:770–779 (1994).

Henrickson, et al., "Recovery of human parainfluenza virus types one and two," *J. Vir. Methods* 46:189–206 (1994).

Henrickson, et al., "Isolation and detection methods useful for efficient recovery of human parainfluenza virus types one and two," *Clin. Infect. Dis.* (submitted).

Karron, et al., "Rapid detection of parainfluenza virus type 3 RNA in respiratory specimens: Use of reverse transcription–PCR–enzyme immunoassay," *J. Clin. Microbiol.* 32:484–488 (1994).

Fan, et al., "Rapid Diagnosis of Human Parainfluenza Virus Type 1 Infection by Quantitative Reverse Transcription–PCR–Enzyme Hybridization Assay," *J. Clin. Microbiol.* 34:1914–1917 (1996).

Henrickson, et al., "Two Distinct Human Parainfluenza Virus Type 1 Genotypes Detected during the 1991 Milwaukee Epidemic," *J. Clin. Microbiol.* 34:695–700 (1996).

*Primary Examiner*—Kenneth R. Horlick
*Assistant Examiner*—Jeffrey Siew
*Attorney, Agent, or Firm*—Quarles & Brady

[57] ABSTRACT

A method for evaluating a sample for the presence or absence of multiple virus infections is disclosed. In one embodiment, this method comprises the step of evaluating a biological sample for nucleic acid sequences complementary to nucleotide primers and probes derived from the sequences of human parainfluenza virus 1, 2 and 3, respiratory syncytial virus A and B and influenza virus, A and B. In another embodiment, the invention is an improved PCR method.

1 Claim, No Drawings

```
                           SEQUENCE LISTING ( 1 ) GENERAL INFORMATION:

( iii ) NUMBER OF SEQUENCES: 65

( 2 ) INFORMATION FOR SEQ ID NO:1:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( ii ) MOLECULE TYPE: oligonucleotide ( xi ) SEQUENCE DESCRIPTION: SEQ ID NO:1:

ATATCAAGGA CTATAAACAT                                                        20

( 2 ) INFORMATION FOR SEQ ID NO:2:

( i ) SEQUENCE CHARACTERISTICS:
              ( A ) LENGTH: 21 base pairs
              ( B ) TYPE: nucleic acid
              ( C ) STRANDEDNESS: single
              ( D ) TOPOLOGY: linear ( ii ) MOLECULE TYPE: oligonucleotide ( xi ) SEQUENCE DESCRIPTION: SEQ ID NO:2:

TTCTGGAGAT GTCCCGTAGG A                                                      21

( 2 ) INFORMATION FOR SEQ ID NO:3:

( i ) SEQUENCE CHARACTERISTICS:
              ( A ) LENGTH: 34 base pairs
              ( B ) TYPE: nucleic acid
              ( C ) STRANDEDNESS: single
              ( D ) TOPOLOGY: linear ( ii ) MOLECULE TYPE: oligonucleotide ( xi ) SEQUENCE DESCRIPTION: SEQ ID NO:3:

TACCTTCATT ATCAATTGGT GATGCAATAT ATGC                                        34

( 2 ) INFORMATION FOR SEQ ID NO:4:
```

```
        (i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:4:

TATTCATCAA ACTTAATCAC TCAAGGATGT G                                      31

(2) INFORMATION FOR SEQ ID NO:5:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:5:

TAAATTCAGA TATGTATCCT GAT                                               23

(2) INFORMATION FOR SEQ ID NO:6:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:6:

ACCTATGACA TCAACGACAA CAGGA                                             25

(2) INFORMATION FOR SEQ ID NO:7:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:7:

TGGCTAAAGA AAAGACAAGT TGTCAATGTC TTAAT                                  35

(2) INFORMATION FOR SEQ ID NO:8:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:8:

GAGACTATTC CAATAACTCA AAATTA                                            26

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
```

(D) TOPOLOGY: linear (ii) MOLECULE TYPE: oligonucleotide (xi) SEQUENCE DESCRIPTION: SEQ ID NO:9:

CCTATGTTGT TCAAGACAAG                                               20

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ile Ser Arg Thr Ile Asn
1               5

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Phe Trp Arg Cys Pro Val Gly
1               5

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Pro Ser Leu Ser Ile Gly Leu Ala Ile Tyr
1               5                   10

(2) INFORMATION FOR SEQ ID NO:13:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Tyr Ser Ser Asn Leu Ile Thr Gln Gly Cys
1               5                   10

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Asn Cys Asp Met Tyr Pro Asp
1               5

(2) INFORMATION FOR SEQ ID NO:15:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:15:

Thr Tyr Asp Ile Asn Asp Asn Arg
1               5

(2) INFORMATION FOR SEQ ID NO:16:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:16:

Trp Leu Lys Lys Arg Gln Val Val Asn Val Leu
1               5                   10

(2) INFORMATION FOR SEQ ID NO:17:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:17:

Glu Thr Ile Pro Ile Thr Gln Asn
1               5

(2) INFORMATION FOR SEQ ID NO:18:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Pro Met Leu Phe Lys Thr
1               5

(2) INFORMATION FOR SEQ ID NO:19:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:19:

ATTTCTGGAG ATGTCCCGTA GGAGAAC                                                       27

(2) INFORMATION FOR SEQ ID NO:20:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:20:

CACATCCTTG AGTGATTAAG TTTGATGAT                                                     29

(2) INFORMATION FOR SEQ ID NO:21:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:21:

TACCTTCATT ATCAATTGGT GATGCAATAT ATG                                                33

(2) INFORMATION FOR SEQ ID NO:22:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:22:

GTCTCATGGA TTCCGATGAT TCACAGCAA                                                     29

(2) INFORMATION FOR SEQ ID NO:23:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:23:

GATGTACGCT GCATCATGCA GAAGCAGA                                                      28

(2) INFORMATION FOR SEQ ID NO:24:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:24:

```
AGGATATGCA TACTGGGAGC ATGTCCAACA CCA                                33

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:25:

TATGGACAAT AATCCTGGTG TTATTATC                                      28

(2) INFORMATION FOR SEQ ID NO:26:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:26:

TAATTTCACT AATGAATTTC CTAAGATC                                      28

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:27:

GTGAATACAA GGCTTCTTAC AATTCAGAGT CAT                                33

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:28:

ACTCTGGACT CAAGAATGAG AAAT                                          24

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:29:

CATATTTGAC AAATAGGCAG GCAT                                          24

(2) INFORMATION FOR SEQ ID NO:30:
```

```
       (i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:30:

CTTCTAACCG AGGTCGAAAC GTA                                                23

(2) INFORMATION FOR SEQ ID NO:31:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:31:

CGTCTACGCT GCAGTCCTCG CTCAC                                              25

(2) INFORMATION FOR SEQ ID NO:32:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:32:

GGCTAAAGAC AAGACCAATC CTGTCACCTC TGACTAA                                 37

(2) INFORMATION FOR SEQ ID NO:33:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:33:

CAGGCCCCCT CAAAGCCGA                                                     19

(2) INFORMATION FOR SEQ ID NO:34:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:34:

CGTCTACGCT GCAGTCCTCG CTCAC                                              25

(2) INFORMATION FOR SEQ ID NO:35:

(i) SEQUENCE CHARACTERISTICS:
            (A) LENGTH: 37 base pairs
            (B) TYPE: nucleic acid
            (C) STRANDEDNESS: single
            (D) TOPOLOGY: linear
```

(ii) MOLECULE TYPE: Oligonucleotide (xi) SEQUENCE DESCRIPTION: SEQ ID NO:35:

GGCTAAAGAC AAGACCAATC CTGTCACCTC TGACTAA                                      37

(2) INFORMATION FOR SEQ ID NO:36:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:36:

AGACCAATCC TGTCACCTCT GAC                                                     23

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:37:

CAACTGGCAA GTGCACCAGC AGA                                                     23

(2) INFORMATION FOR SEQ ID NO:38:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:38:

AGTGAGCGAG GACTGCAGCG TAGACGCTTT GTCCA                                        35

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:39:

AGACCAATCC TGTCACCTCT GAC                                                     23

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:40:

CTGTTGTATA TGAGGCCCAT                                                          20

(2) INFORMATION FOR SEQ ID NO:41:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:41:

AGTGAGCGAG GACTGCAGCT GCAGCGTAGA CGCTTTGTCC A                                   41

(2) INFORMATION FOR SEQ ID NO:42:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:42:

ATGGCCATCG GATCCTCAAC TCACTC                                                   26

(2) INFORMATION FOR SEQ ID NO:43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:43:

TCATGTCAGC TATTATGGAG CTGTT                                                    25

(2) INFORMATION FOR SEQ ID NO:44:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:44:

AGCCAATTCG AGCAGCTGAA ACTGCGGTGG GAGTC                                         35

(2) INFORMATION FOR SEQ ID NO:45:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:45:

ATGGCCATCG GATCCTCAAC TCACTC                                                   26

(2) INFORMATION FOR SEQ ID NO:46:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:46:

TCATGTCAGC TATTATGGAG CTGTT                                                          25

(2) INFORMATION FOR SEQ ID NO:47:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:47:

TATCCCAATT TGGTCAAGAG CACCGATTAT CACCAG                                               36

(2) INFORMATION FOR SEQ ID NO:48:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:48:

ACAATCTAAA ACAACAACTC TATGC                                                          25

(2) INFORMATION FOR SEQ ID NO:49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:49:

GTGTATTTGC TGGATGACAG                                                                20

(2) INFORMATION FOR SEQ ID NO:50:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:50:

ATGCATAACT ATACTCCATA GTCCAGATGG AGCCTGAA                                             38

(2) INFORMATION FOR SEQ ID NO:51:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO:51:

ATGAACAGTT TAACATTACC AAGTGA                                          26

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:52:

CCACGATTTT TATTGGATGC                                                 20

(2) INFORMATION FOR SEQ ID NO:53:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:53:

GTGTCATGCT ATGGCAAAAC TAAATG                                          26

(2) INFORMATION FOR SEQ ID NO:54:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:54:

AACTAACCCA TCCAAACTAA GCTATTCCTC AA                                   32

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:55:

GTGTATTTGC TGGATGACAG                                                 20

(2) INFORMATION FOR SEQ ID NO:56:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:56:

```
CAAACAACAG TGCTCAACAG TTAAGAAGGA GCTAATCCA                                    39

(2) INFORMATION FOR SEQ ID NO:57:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:57:

CTCTTAATCA TCTAATTGTA ATATCCT                                                 27

(2) INFORMATION FOR SEQ ID NO:58:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:58:

TTAGTGTAAC TTTGTGATTG GCAGAG                                                  26

(2) INFORMATION FOR SEQ ID NO:59:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:59:

TGGCAATGAT AATCTCAACC TCTCTCATAA TTGCAGC                                      37

(2) INFORMATION FOR SEQ ID NO:60:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:60:

AGGAGTAAAG TTACGCAAT                                                          19

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:61:

TGATTACTTA TCATATACTT G                                                       21

(2) INFORMATION FOR SEQ ID NO:62:
```

-continued (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:62:

AAGATCCAAA TGGCATCGGA TAATA                                    25

(2) INFORMATION FOR SEQ ID NO:63:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:63:

TAATTTCACT AATGAATTTC CTAAGATC                                 28

(2) INFORMATION FOR SEQ ID NO:64:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:64:

AAGATCCAAA TGGCATCGGA TAATA                                    25

(2) INFORMATION FOR SEQ ID NO:65:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:65:

TAATTTCACT AATGAATTTC CTAAGATC                                 28

MULTIPLEX PCR ASSAY USING UNEQUAL PRIMER CONCENTRATIONS TO DETECT HPIV 1,2,3 AND RSV A,B AND INFLUENZA VIRUS A, B

This application is a continuation-in-part of 08/552,907 filed Nov. 3, 1995 now U.S. Pat. No. 5,744,299 Apr. 28, 1998.

FIELD OF THE INVENTION

In general, the present invention relates to assays for human parainfluenza virus combined with assays for other disease-causing viruses. In particular, the present invention relates to amplification-based and non-amplification-based assays for parainfluenza virus-1, 2 and 3 combined with assays for respiratory syncytial virus A and B and influenza virus A and B.

BACKGROUND

Human parainfluenza virus type one (HPIV-1) is a major cause of lower respiratory tract infections (LRI) in infants, young children, and the immunocompromised (Henrickson, K. J., "Lower respiratory viral infections in immunocompetent children," pp. 59–96, In Aronoff SC (ed), *Advances in Pediatric Infectious Diseases*. Mosby-Year Book, Chicago, Ill., 1994; Henrickson, K. J., et al., Parainfluenza. In: Mandell, Bennet D. (ed) *Principles and Practices of Infectious Diseases*, Edition 4, Churchill Livingston, N.Y., 1994). This virus has world-wide distribution and probably contributes significantly to childhood mortality in the developing world (Henrickson, K. J., supra, 1994; Henrickson, K. T., et al., supra, 1994). In the United States, we have demonstrated significant morbidity and cost attributable to HPIV-1 epidemics (Henrickson, K. J., et al., "Epidemiology and cost of human parainfluenza virus types one and two infections in young children," *Clin. Infect. Dis.* 18:770–9, 1994). During these epidemics, approximately 100,000 children less than five years of age are seen in emergency rooms and approximately 35,000 are hospitalized at a combined cost of approximately $90,000,000 (Henrickson, K. J., et al., supra, 1994). Currently, there is no specific therapy or vaccine for any HPIV.

We recently reported that HPIV-1 collected over a 26-year period in a single city demonstrated different genotypes and that one of these genotypes (A) had genotype-specific antigenic markers detectable using MAbs and human sera (Henrickson, K. J., "Monoclonal antibodies to human parainfluenza virus type 1 detect major antigenic changes in clinical isolates," *J. Infect. Dis.* 164:1128–34, 1991; Henrickson, K. J., et al., "Genetic variation and evolution of human parainfluenza virus type 1 hemagglutinin neuraminidase: Analysis of 12 clinical isolates," *J. Infect. Dis.* 164:1128–34, 1992). Subsequently, others have found similar antigenic changes in HPIV-1, and one report failed to find genotypes or antigenic markers over a nine-year period (Komada, H., et al., "Antigenic diversity of human parainfluenza virus type 1 isolates and their immunological relationship with Sendai virus revealed by monoclonal antibodies," *J. Gen. Virol.* 73:875–84, 1992; Hetherington, S. V., et al., "Human parainfluenza virus type 1 evolution combines cocirculation of strains and development of geographically restricted lineages," *J. Infect. Dis.* 169:248–52, 1994).

HPIV-2 outbreaks occur either biennially or yearly (B. Murphy, et al., "Seasonal pattern in childhood viral lower respiratory tract infections in Melbourne," *Med. J. Australia* 1:22–24, 1980; M. A. Downham, et al., "Diagnosis and clinical significance of parainfluenza virus infections in children," *Arch. Dis. Child* 49:8–15, 1974; P. Wright, "Parainfluenza viruses." In: R. B. Belshe ed. Textbook of Human Virology. Littleton, Mass.: PSG Publishing pp. 299–310, 1984), the majority of them appear in fall to early winter. HPIV-2 is a frequent cause of croup. It causes LRI much less frequently than HPIV-1 and HPIV-3, although the difference may be attributable to the difficulties with viral detection. Approximately 60% of HPIV-2 infections take place in the first 5 years of life; the peak incidence occurs in the second year, but significant numbers of infants are infected under 1 year of age. Although frequently overshadowed by HPIV-1 and HPIV-3, HPIV-2 can be predominant in some years (K. J. Henrickson, et al., "Epidemiology and cost of infection with human parainfluenza virus types 1 and 2 in young children," *Clin. Infect. Dis.* 18:770–779, 1994).

HPIV-3 is unique among the parainfluenaza viruses in its propensity to infect young infants less than 6 months of age. LRI due to HPIV-3 causes approximately 20,000 infants and children to be hospitalized each year in the United States. About 40% of HPIV-3 infections in the first 12 months of life lead to bronchiolitis and pneumonia. It is second only to RSV as a cause of LRI in neonates and young infants. Although endemic throughout the world, this virus also occurs in spring epidemics in North America.

Recent molecular analyses of all four serotypes has revealed more antigenic and genetic heterogeneity than had been appreciated previously (K. J. Henrickson, "Monoclonal antibodies to human parainfluenza virus type 1 detect major antigenic changes in clinical isolates," *J. Infect. Dis.* 164:1128–1134, 1991; K. J. Henrickson, et al., "Genetic variation and evolution of human parainfluenza virus type 1 hemagglutinin neuraminidase: Analysis of 12 clinical isolates," *J. Infect. Dis.* 166:995–1005, 1992; K. Prinoski, et al., "Evolution of the fusion protein gene of human parainfluenza virus 3," *Virus Res.* 22:55–69, 1992; M. Tsurudome, et al., "Extensive antigenic diversity among human parainfluenza type 2 virus isolates and immunological relationships among paramyxoviruses revealed by monoclonal antibodies," *Virology* 171:38–48, 1989; T. I. Yorlova, et al., "Studies of natural population variability of parainfluenza viruses during their epidemic circulation," *Acta Virol.* 25:64–70, 1991; K. L. van Wyke Coelingh, et al., "Antigenic variation in the hemagglutinin-neuraminidase protein of human parainfluenza type 3 virus," *Virology* 143:569–582, 1985; H. Komada, et al., "Strain variation in parainfluenza virus type 4," *J. Gen. Virol.* 71:1581–1583, 1990; H. Komada, et al., "Antigenic diversity of human parainfluenza virus type 1 isolates and their immunological relationship with Sendai virus revealed by monoclonal antibodies," *J. Gen. Virol.* 73:875–884, 1992). It appears that all four major HPIV types have virus subgroups that have unique antigenic and genetic characteristics. This includes variability even within HPIV-4 subtypes (H. Komada, et al., supra, 1990). The evolution of these viruses appears to be similar in pattern to influenza B. Most HPIV strains have type-specific antigens that will react in polyclonal serologic testing as previously described. However, HPIV-1 and HPIV-3 have subgroups (A and B) showing progressive antigenic changes (K. J. Henrickson, supra, 1991; K. Prinoski, et al., supra, 1992). Furthermore, HPIV-1 strains isolated over the past 10 years show persistent antigenic and genetic differences compared to the 1957 type strain (K. J. Henrickson, supra, 1991; K. J. Henrickson, supra, 1992; H. Komada, et al., supra, 1992). Because of this, standard reference sera prepared to HPIV isolates from the 1950s, or antigen prepared from these same "type" strains, may not react in current serologic assays.

Detection methods for human parainfluenza viruses 1, 2 and 3 currently include standard viral culture of the suspected infected fluid or tissue. This is a slow and expensive process that may take up to ten days to isolate the virus, and in the best hands, may have a sensitivity of only 40–50%. Direct antigen detection using immunofluorescence is also available both in this country and throughout the world, but the detection rate for HPIV by this method is highly variable with sensitivities averaging only in the 50–70% range and specificities being in the 80–90% range.

A published method concerning the use of an RT-PCR ELISA for the detection of a human parainfluenza virus type-3 was disclosed by Karron in the *Journal of Clinical Microbiology* (February, 1994, pp. 484–488) entitled "Rapid detection of parainfluenza virus type 3 RNA in respiratory specimens: Use of a reverse transcription-PCR-enzyme-immunoassay." The methods described in this paper are specific for an assay to detect human parainfluenza virus type 3 using specific sequences from the HN gene of HPIV-3. However, their methodology is different from the present invention because the present invention allows for the detection of HPIV-1, 2, and 3 in a single test. Furthermore, the present invention allows for the quantitation of HPIV genomic RNA in a clinical sample.

The published method concerning the use of an RT-PCR-ELISA for the detection of influenza A virus was disclosed by Thomas Cherian in the Journal of Clinical Microbiology (March, 1994, page 623–628) entitled "Use of PCR-enzyme immunoassay for identification of influenza A virus matrix RNA in clinical samples negative for cultivable virus." The methods described in this paper are specific for an assay to detect influenza A virus using specific sequences from the matrix protein gene. The Cherian method does not allow for the quantitation of influenza A and B virus genomic RNA in a clinical sample.

A published method concerning the use of an RT-PCR ELISA for the detection of respiratory syncytial virus was disclosed by Freymuth in the Journal of Clinical Microbiology (December, 1995, page 3352–3355) entitled "Detection of respiratory syncytial virus by reverse transcription PCR and hybridization with a DNA enzyme immunoassay." The methods described in this paper are specific for an assay to detect RSV using specific sequences from the 1B and N gene. This method does not allow for the detection of RSV, influenza virus, and HPIV in a single test or allow for the quantitation of RSV genomic RNA in a clinical sample.

A fast and efficient method for detection and quantitation in a biological sample of human parainfluenza virus 1, 2 and 3 along with other disease-causing viruses, such as respiratory syncytial virus A and B and influenza virus A and B, is needed.

SUMMARY OF THE INVENTION

In one embodiment, the present invention is a methodic for evaluating a biological sample for the presence or absence of multiple viruses by use of an amplification reaction, such as the polymerase chain reaction. Preferably, this method comprises the steps of isolating RNA from a biological sample and creating cDNA from the isolated RNA. The cDNA is exposed to oligonucleotide primers. If the assay is designed to detect human parainfluenza virus-1 infection, the primer is selected from the group consisting of SEQ ID NOs:1–9. In this embodiment of —he present invention, one primer will be in the same 5'-3' orientation presented in SEQ ID NOs:1–9 and the other primer will be in the inverse complement orientation. The exposure is under conditions in which the primers will amplify a human parainfluenza virus-1 sequence if the sequence is present. The sample is then examined to determined whether an amplification product exists. The presence of an amplification product indicates that the sample contained human parainfluenza virus-1.

The present invention additionally comprises exposing the cDNA to oligonucleotide primers designed to detect additional viruses. These viruses are selected from the group consisting of parainfluenza virus-2 and 3, respiratory syncytial virus A and B, and influenza virus A and B. Preferred oligonucleotides designed to detect these additional viruses are described in Tables 5, 7 and 8. Preferably, SEQ ID NOs:30, 31, 33, 34, 36, 37, 39, 40, 42, 43, 45, 46, 48, 49, 51, 52, 54, 55, 57 and 58 are preferred primers for respiratory syncytial viruses A and B and influenza viruses A and B. Tables 5, 7 and 8 also describe suitable probes designed to detect amplification products. Preferably, SEQ ID NOs:32, 35, 38, 41, 44, 47, 50, 53, 56 and 59 are preferred probes for respiratory syncytial virus A and B and influenza virus A and B.

The present invention is also a method for directly evaluating a biological sample for the presence or absence of human parainfluenza virus-1 infection along with infections caused by viruses selected from the group consisting of human parainfluenza virus-2 and 3, respiratory syncytial virus A and B, and influenza virus A and B. This method comprises the steps of isolating RNA from a biological sample. This RNA is then exposed to a probe selected from the group of SEQ ID NOs:1–9 and complements of SEQ ID NOs:1–9 for detection of human parainfluenza virus-1. This exposure is under conditions that allow a hybridization reaction to occur if the probe is in the presence of a complementary nucleic acid. The sample is then examined for the presence or absence of a hybridization product. The presence of a hybridization product indicates that the sample contains human parainfluenza virus-1 nucleic acid and that the patient is infected with parainfluenza virus-1.

Oligonucleotide primers taken from Tables 5, 7 and 8 (as described above) can be used to examine the biological sample for the additional viruses.

In a preferred embodiment of the present invention, the amplification product described above is anchored onto a solid support, such as a microtiter plate, and detected via an enzyme-labeled probe. We have named this method of analyzing a PCR product "PCR-EHA" for PCR-enzyme hybridization assay.

The present invention is also a PCR-ELISA-based method of detecting multiple virus infection of a biological sample comprising the steps of isolating RNA from a biological sample, creating cDNA from the isolated RNA and exposing the cDNA to a primer pair specific for a human parainfluenza sequence and primers specific for respiratory syncytial virus A and B sequence or influenza A and B sequence under conditions permitting an amplification reaction. An amplification product will be formed if the sample contains the viruses. The results of the amplification procedure are exposed to a protein-linked oligonucleotide probe, wherein the probe is of a sequence identical to a virus-specific sequence and wherein the protein-linked probe is attached to a solid support. One then determines whether the amplification product has hybridized to the oligonucleotide.

In another embodiment, the present invention is an improved method of PCR. In one embodiment, the method comprises the step of supplying primers to the reaction in non-equivalent concentrations. Preferable concentrations include an approximately 50 $\mu$M:25 $\mu$M ratio, 25 $\mu$M:50 $\mu$M ratio, 12.5 $\mu$M:50 $\mu$M ratio or 12.5 $\mu$M:25 $\mu$M ratio of 5' primer to 3' primer.

In another embodiment, the present invention is also an improved PCR reaction comprising the step of multiply denaturing the sample. Preferably, the sample is denatured at least twice for 5 minutes at 95° C.

It is an object of the present invention to detect human parainfluenza virus-1, 2 and 3, respiratory syncytial virus A and B, and influenza virus A and B sequences in a single tube assay.

It is another object of the present invention to detect hemagglutinin neuraminidase sequences of HPIV-1, 2, or 3, influenza virus A matrix (M) gene sequences, influenza virus B nonstructural (NS) gene sequences, RSV A 1B, nucleocapsid and fusion (F) gene sequences, and RSV B 1B, nucleocapsid, and attachment (G) gene sequences.

Other objects, features and advantages of the present invention will become apparent after examination of the specification and claims.

DESCRIPTION OF THE INVENTION

In General

In one embodiment, the present invention is an assay for human parainfluenza-1 (HPIV-1) combined in an assay for at least one other virus. Preferably, this assay examines a biological sample for the presence or absence of parainfluenza-1, 2 and 3, respiratory syncytial virus A and B and influenza virus A and B.

In one aspect, the present invention involves performing an amplification reaction. Preferably, the amplification reaction is the PCR reaction. However, there are other suitable amplification techniques such as CPR (Cycling Probe Reaction), bDNA (Branched DNA Amplification), SSR (Self-Sustained Sequence Replication), SOA (Strand Displacement Amplification), QBR (Q-Beta Replicase), Re-AMP (Formerly RAMP), NASBA (Nucleic Acid Sequence Based Amplification), RCR (Repair Chain Reaction), LCR (Ligase Chain Reaction), TAS (Transorbtion Based Amplification System), and HCS (amplifies ribosomal RNA).

In one embodiment of the invention, this assay comprises the steps of exposing a cDNA created from RNA isolated from a biological sample to oligonucleotide primers chosen from the group described below in Tables 1, 5, 7 and 8. The sample may then be examined for the presence of an amplification product. SEQ ID NOs:30, 31, 33, 34, 36, 37, 39, 40, 42, 43, 45, 46, 48, 49, 51, 52, 54, 55, 57 and 58 are preferable primers.

In another embodiment, the sequences in Tables 1, 5, 7 and 8 may be used to design a probe which would be used to hybridize to nucleic acid sequences that are diagnostic for the viruses. In a preferable embodiment, SEQ ID NOs:32, 35, 38, 41, 44, 47, 50 53, 56 and 59 are preferable probes.

In another embodiment, the present invention is an assay for multiple viruses, preferably human parainfluenza virus-1, 2 and 3, respiratory syncytial virus A and B and influenza virus A and B. This assay comprises the steps of exposing a cDNA created from RNA isolated from a biological sample to oligonucleotide primers specific for the viruses. This exposure is under conditions capable of amplifying a the virus-specific sequences if the sequences are present. The products of the PCR reaction are then exposed to a protein-linked oligonucleotide probe that has been attached to a solid support via the protein. One then determines whether the amplification product has bound to the solid support, preferably by use of enzymatic labels.

Kits

In another embodiment, the present invention is a kit for assaying human parainfluenza virus type 1 and other viruses, preferably human parainfluenza virus-2 and -3, respiratory syncytial virus A and B and influenza virus A and B. In a preferred embodiment, the kit comprises a pair of primers selected from SEQ ID NOs:1–9 and at least one pair of primers designed to amplify respiratory syncytial virus A or B or influenza virus A or B. In a more preferred embodiment of the kit, the kit additionally comprises primers specific for human parainfluenza virus-2 and a pair of primers specific for human parainfluenza virus-3. In a most preferred embodiment of the kit, the kit additionally comprises primers selected from SEQ ID NOs:30, 31, 33, 34, 36, 37, 39, 40, 42, 43, 45, 46, 48, 49, 51, 52, 54, 55, 57 and 58 specific for respiratory syncytial virus A and B and influenza virus A and B.

In another embodiment, the kit additionally comprises oligonucleotide probes specific for parainfluenza virus-1 and probes specific for human parainfluenza virus-2 or 3, respiratory syncytial virus A or B, or influenza virus A or B. In a more preferred embodiment of the kit, the kit additionally comprises probes selected from SEQ ID NOs:32, 35, 38, 41, 44, 47, 50 53, 56 and 59 specific for respiratory syncytial virus A and B and influenza virus A and B.

HPIV-1 Probes and Primers

The present invention requires the use of a probe or primer pairs that are diagnostic for HPIV-1. To develop these probes or primers, one must first determine what genetic sequences are conserved between the many strains of HPIV-1. If one were to use a sequence derived from only a few strains, one would risk not detecting an HPIV-1 strain that had mutated slightly from this group.

We had previously investigated genetic diversity in HPIV-1 by sequencing the hemagglutinin neuraminidase (HN) gene of 12 clinical isolates (Henrickson and Savatski, J. Infect. Dis. 166[5]:995–1005, 1992). HN is an important surface protein for this virus. Additionally, we were able to combine 13 HN sequences obtained from GenBank. (The GenBank location of the sequences we examined is listed in Appendix 1.) To this group, we added 15 isolates of HPIV-1 that we collected in 1991 during a single fall epidemic.

We compared these 15 new sequences to the known HPIV-1 sequences and looked for highly conserved nucleotide sequences. Our criteria was that the sequence should be greater than or equal to 20 nucleotides in length and contain no nucleotide changes.

Table 1 describes the 9 highly conserved nucleotide sequence regions that we obtained. Table 2 describes the predicted amino acid sequences derived from the conserved nucleotide sequences in Table 1. (The bases and amino acid designations correspond to the numbering system for the HN gene described in Henrickson and Savatski, *J. Infect. Dis.* 116[5]:995–1005, 1992).

still preferred. Preferably in both cases, the fragment should exceed 150 nucleotides.

Additionally, the primer pair should be in an orientation that permits amplification. The forward primer should be in the 5'-3' orientation depicted in Table 1. The reverse primer should be in an inverse complement orientation. The primers listed below in the Example (SEQ ID NOs:19 and 20) are examples of suitably oriented primers. One primer (SEQ ID NO:19) is the 5'-3' orientation of a portion of SEQ ID NO:2 depicted above. The other primer (SEQ ID NO:20) is the inverse complement orientation of a portion of SEQ ID NO:4.

Additionally, the primer should be chosen so that the two primers are not complementary at the 3 ends. This situation would lead to a hybridization reaction between the primers before the primers hybridize to the substrate material. A complementary region of equal to or greater than 2 nucleotides will cause an unwanted primer hybridization. Preferably, there will be no complementary region at the 3' end.

TABLE 1

| HN base pair location: | Sequence: |
|---|---|
| 1. 342 - 361: | 5'-ATATCAAGGACTATAAACAT (SEQ ID NO: 1) |
| 2. 528 - 548: | 5'-TTCTGGAGATGTCCCGTAGGA (SEQ ID NO: 2) |
| 3. 640 - 673: | 5'-TACCTTCATTATCAATTGGTGATGCAATATATGC (SEQ ID NO: 3) |
| 4. 675 - 705: | 5'-TATTCATCAAACTTAATCACTCAAGGATGTG (SEQ ID NO: 4) |
| 5. 754 - 776: | 5'-TAAATTCAGATATGTATCCTGAT (SEQ ID NO: 5) |
| 6. 798 - 822: | 5'-ACCTATGACATCAACGACAACAGGA (SEQ ID NO: 6) |
| 7. 1173 - 1207: | 5'-TGGCTAAAGAAAAGACAAGTTGTCAATGTCTTAAT (SEQ ID NO: 7) |
| 8. 1251 - 1276: | 5'-GAGACTATTCCAATAACTCAAAATTA (SEQ ID NO: 8) |
| 9. 1734 - 1753: | 5'-CCTATGTTGTTCAAGACAAG (SEQ ID NO: 9) |

TABLE 2

| | HN gene location: | Sequence: |
|---|---|---|
| 1. | 96 aa-101 aa: | 5'-ISRTIN (SEQ ID NO: 10) |
| 2. | 158 aa-164 aa: | 5'-FWRCPVG (SEQ ID NO: 11) |
| 3. | 196 aa-205 aa: | 5'-PSLSIGLAIY (SEQ ID NO: 12) |
| 4. | 207 aa-216 aa: | 5'-YSSNLITQGC (SEQ ID NO: 13) |
| 5. | 234 aa-240 aa: | 5'-NCDMYPD (SEQ ID NO: 14) |
| 6. | 248 aa-255 aa: | 5'-TYDINDNR (SEQ ID NO: 15) |
| 7. | 373 aa-383 aa: | 5'-WLKKRQVVNVL (SEQ ID NO: 16) |
| 8. | 399 aa-406 aa: | 5'-ETIPITQN (SEQ ID NO: 17) |
| 9. | 560 aa-565 aa: | 5'-PMLFKT (SEQ ID NO: 18) |

Therefore, to practice the present invention, one preferably uses a probe or primer pair derived from SEQ ID NOs:1–9. The following criteria are useful in deriving such a probe or primer.

A. Probe

A probe suitable to hybridize with a HN gene sequence will be at least 20 nucleotides in length. Preferably, a probe will be 30 nucleotides in length, and most preferably a probe will be at least 35 nucleotides in length. This length may be taken from any area of the sequence. The probe should preferably have a GC content of approximately 50%. SEQ ID NO:1 is not a preferable probe because the GC composition is too low.

B. Primers

To derive primers from the Table 1 sequences, one must first choose sequences that when amplified would produce a DNA segment of sufficient length. For the PCR-ELISA technique that we described below in the Examples, one would need a DNA segment of at least 100 nucleotides. If one wishes to visualize a PCR fragment on electrophoretic gel, a smaller fragment would suffice. However, for optimum PCR amplification, a fragment of 100 nucleotides is still preferred.

Also preferred are primers that do not have internal complementary segments that allow formation of hairpins.

The primers should be at least 20 nucleotides in length. This 20 nucleotides may be chosen from within the entire length of the sequence reported. For example, a 20 nucleotide length from SEQ ID NO:8 may start with the initial GAG or may start with the fifth nucleotide C. Primers may be longer than 20 nucleotides in length if one wishes.

As described above for probe selection, a GC percentage of approximately 50% is preferred. SEQ ID NO:1 is not a preferred primer because the GC concentration is too low.

The Example below describes a preferable method of isolating nucleic acid suitable to be amplified from a nasal wash. Briefly, the 1–2 ml specimens were emptied into transport tubes containing 2 ml of minimal essential medium supplemented with bovine serum albumin, amphotericin B, penicillin G, and gentamicin. These specimens are centrifuged and the supernatants divided and refrigerated.

RNA is preferably isolated from these supernatant samples by adding a guanidinium solution described below in the Examples. Other methods known in the art of isolating RNA would also be suitable.

The following are preferred primer pairs for PCR reactions. The numbers in Table 3 and 4 refer to the SEQ ID NO. For example, "2" indicates SEQ ID NO:2.

TABLE 3

| GROUP A | GROUP B | GROUP C | GROUP D | GROUP E | GROUP F | GROUP G |
|---------|---------|---------|---------|---------|---------|---------|
| 2 + 3   | 3 + 5   | 4 + 5   | 5 + 7   | 6 + 7   | 7 + 8   | 8 + 9   |
| 2 + 4   | 3 + 6   | 4 + 6   | 5 + 8   | 6 + 8   | 7 + 9   |         |
| 2 + 5   | 3 + 7   | 4 + 7   | 5 + 9   | 6 + 9   |         |         |
| 2 + 6   | 3 + 8   | 4 + 8   |         |         |         |         |
| 2 + 7   | 3 + 9   | 4 + 9   |         |         |         |         |
| 2 + 8   |         |         |         |         |         |         |
| 2 + 9   |         |         |         |         |         |         |

HN-specific oligonucleotide primer pairs and probes that are preferred for PCR-EHA are listed below in Table 4.

TABLE 4

| GROUP A | | GROUP B | | GROUP C | | GROUP D | | GROUP E | | GROUP F | |
|---|---|---|---|---|---|---|---|---|---|---|---|
| Primer | Probe | Primer | Probe | Primer | Probe | Primer | Probe | Primer | Probe | Primer | Probe |
| 2 + 4 | 3 | 3 + 5 | 4 | 4 + 6 | 5 | 5 + 7 | 6 | 6 + 8 | 7 | 7 + 9 | 8 |
| 2 + 5 | 3, 4 | 3 + 6 | 4, 5 | 4 + 7 | 5, 6 | 5 + 8 | 6, 7 | 6 + 9 | 7, 8 | | |
| 2 + 6 | 3, 4, 5 | 3 + 7 | 4, 5, 6 | 4 + 8 | 5, 6, 7 | 5 + 9 | 6, 7, 8 | | | | |
| 2 + 7 | 3, 4, 5, 6 | 3 + 8 | 4, 5, 6, 7 | 4 + 9 | 5, 6, 7, 8 | | | | | | |
| 2 + 8 | 3, 4, 5, 6, 7 | 3 + 9 | 4, 5, 6, 7, 8 | | | | | | | | |
| 2 + 9 | 3, 4, 5, 6, 7, 8 | | | | | | | | | | |

Human Parainfluenza Probes and Primers for PCR-EHA-based Assay

The present invention is also a PCR-EHA-based method of assaying a biological sample for any type human parainfluenza. This assay depends on a protein-linked oligonucleotide specific for a human parainfluenza gene sequence linked to a solid support via the protein molecule.

The method begins with exposing a biological sample to a primer pair specific for any human parainfluenza gene. We have described above how to isolate a primer pair specific for the HN gene. The human parainfluenza genome is known to comprise a variety of genes and many of these would be diagnostic for human parainfluenza. One would first obtain a nucleotide sequence of a human parainfluenza gene that is diagnostic for human parainfluenza as opposed to other infectious agents and cellular components. This could be facilitated by searching gene banks for any known sequence similar to the candidate sequence. If no matches are found, then the candidate sequence is likely to be specific to HPIV.

One would then construct a suitable primer pair from this gene sequence. Criteria listed above will be useful in constructing such a primer pair. One would then expose RNA isolated from a suitable biological sample to this primer pair under conditions suitable for PCR amplification.

Separately, one would obtain a probe, using the criteria described above, specific for a human parainfluenza gene sequence. This probe should be attached to a protein molecule capable of binding a solid support. We have described above a procedure wherein BSA is attached to an oligonucleotide and used to bind a solid support. However, other protein molecules may be equally suitable. To determine whether a protein molecule is as suitable for the present invention as BSA, one would run a reaction with a candidate protein in parallel to a reaction with BSA and determine whether the candidate protein linked oligonucleotides attached to the plate with the same efficiency as the BSA-linked oligonucleotides.

The protein-linked oligonucleotide is then attached to a solid support in preparation for a PCR-EHA assay as described above. One then determines whether the amplification product is present, thus indicating that the biological sample is infected with human parainfluenza virus.

HPIV-1 Assay

To perform the method of the present invention, one must first select a probe and primer pair as described above and expose the cDNA described above to the primer pair. After amplification, the PCR product is dejected with the corresponding probe.

Biological Sample

The probe or primers derived from the Table 1 conserved sequences are exposed to a biological sample that may contain HPIV-1 virus. This biological sample is preferably a nasal wash made from nasal secretions. Preferably, one would prepare the nasal wash by standard methods known to one of skill in the art. Preferably, as described in Henrickson, J. Viol. Methods, 46:189–206, 1994 or Hall and Douglas, J. Infect. Dis., 131:1–5, 1975.

However, other biological fluids such as nasal aspirates or pleural fluid, preferably respiratory fluids, would also be suitable. Other body fluids such as blood or spinal fluid would all be suitable for the present invention.

The present invention is especially useful for the diagnosis of HPIV-1 in immunocompromised children or adults. These patients might preferably be diagnosed by broncho alveolar lavage.

Reverse Transcription Reaction

Once RNA is isolated from the biological sample, one needs to perform a reverse transcription reaction to create a cDNA template for the primers.

A suitable reverse transcription reaction requires that the RNA sample be exposed to reverse transcriptase enzyme and deoxyribonucleotides so that a cDNA molecule may be created that corresponds to the initial RNA molecule.

Preferably, a reverse transcription reaction is performed as described below in the Examples.

A. PCR Reaction

Preferably, one would choose to use a pair of primers and examine the final product for the presence of a PCR amplification product. This examination could involve examining the products of the reaction on an electrophoretic gel and determining whether an amplified product of the appropriate size had been created. One of skill in the art of molecular biology will be aware of many protocols designed to optimize PCR reactions. Particularly useful protocols are described in *PCR Protocols*, Ed. M. Innis, et al. Academic Press, San Diego.

Most preferably, the PCR reaction will be coupled to an EHA procedure. As described below, one would anchor the PCR amplification product to a solid support and examine the support for the presence of the PCR product. This procedure could be done in several ways. We will describe two of the most preferable ways below.

PCR-EHA Method A. In this method, one first attaches the amplified product to a solid support, such as a microtiter dish. For example, a streptavidin-coated plate may be provided. One of the selected primers may be attached to a biotin molecule so that an amplification product will be labelled with biotin and bind to the streptavidin plate.

The plate and product are then exposed to an HN-specific oligonucleotide probe containing a segment of the HN sequence. This probe is attached to a marker enzyme, such as horseradish peroxidase (HRP), which may be detected via its enzymatic properties.

This protocol is described in detail in the Examples below.

PCR-EHA Method B. In PCR-EHA method B, one would attach a protein molecule capable of binding to the solid support, such as BSA, to an HN-specific oligonucleotide probe. The plate is coated with these protein-attached oligonucleotides that are available to hybridize with an amplified product. This amplified product is preferably attached to a label molecule, such as biotin, that is capable of being detected. In one embodiment, the biotin-labelled PCR product may be complexed to a streptavidin-horse radish peroxidase conjugate. One may then detect this complex with the appropriate substrate. A preferred method of performing this method is described below:

One must first derivitize the 5' phosphorylated oligonucleotide probe (oligolink derivitization reagent, PIERCE). Preferably, one would place 20 ug/ul of 5'-phosphorylated oligonucleotide in a clean 1.5 ul microcentrifuge tube. Remove 200 ul of the derivitization reagent and transfer to a vial containing EDC (ethyl-3[3-dimethyl-aminopropyl] carbodiamide).

Centrifuge the tube 3 seconds in a microcentrifuge to collect reactants in the bottom of the tube. Incubate the tube at 50° C. for 30 minutes with constant mixing.

Resuspend the OligoLink™ matrix by vortexing until no solid is visible in the bottom of the tube. To an assembled spin column add 160 ul of matrix. Place the column in a microcentrifuge tube and centrifuge briefly (5 seconds) to remove the excess water. After spinning, carefully push the bottom cap onto the column. Discard the water from the collection tube.

Following the incubation period, add 81 ul OligoLink™ binding buffer to the tube containing the derivitization oligonucleotide. Mix well and transfer the entire contents to the spin column containing the OligoLink™ matrix. Screw the top cap onto the spin column and invert the column to mix the reactants. Agitate the tightly capped spin column at room temperature for 15 minutes. Following the 15 minute incubation period, spin the column for 2 seconds with caps in place to collect the reactants in the bottom of the column. Carefully remove top and bottom caps. Place the spin column in a collection tube and centrifuge for 10 seconds.

To the spin column add 500 ul OligoLink™ binding buffer. Spin for 10 seconds. Wash the OligoLink™ matrix by adding 500 ul ethanol wash buffer. Spin 10 seconds. To spin the column and another 500 ul of ethanol wash buffer, followed by 1.0 ul of DTT solution. Replace the top cap on the spin column and invert several times to suspend the matrix in the reductant. Incubate 10 minutes with occasional mixing.

Following the reduction step, spin column 2 seconds with caps in place to collect reactants in the bottom of the column then remove top and bottom caps. Place spin column in a collection tube and spin for 10 seconds. Wash the excess DTT from the column by adding 500 ul ethanol wash buffer. Spin 10 seconds.

Repeat the ethanol wash 3 more times using 500 ul of ethanol wash buffer each time. Add 160 ul $H_2O$ (preheated to 55° C.), and incubate the entire column at 55° C. for 5 minutes. Remove caps and place the column in a clean 1.5 ml collection tube. Spin the column for 20 seconds. Discard eluate.

One should then prepare a maleimide activated BSA/oligonucleotide probe complex (Imject Maleimide Activated Bovine Serum Albumin™, Pierce). Add 4 ml $H_2O$ to 2 mg activated BSA. Immediately mix the oligo and 0.2 ml BSA, incubate at room temperature for 2 hours and hold at −20° C.

To coat the ELISA plate, one may follow the following procedure. Preferably Costar, EIA/RIA plates, Medium Bind-in 3591, are obtained. Make up a solution containing 30 ul oligo-BSA complex in 15 ml coating buffer. (Coating buffer is 0.2M Carbonate-Bicarbonate buffer, pH 9.4). Add 100 ul/well of this solution and incubate at 4° C. overnight. The next morning, empty plate and wash with PBS 3 times.

To block the ELISA plate, one would preferably use the following procedure: Add 300 ul/well blocking solution. (Blocking solution is 5× Denhardt's solution, 1% gelatin [EIA grade, BIORAD], 250 ug/ml herring sperm DNA.) Incubate overnight at 4° C. Remove blocking solution by aspiration next morning.

One then performs an enzyme hybridization assay. Preferably, add 70 ul/well of premixed solution for solution hybridization. Mix 5 ul denatured PCR product (denature at 95° C., 5 minutes, keep on ice, 10 minutes) and 65 ul hybridization buffer. Incubate at 42° C. 1 hour.

A preferable hybridization buffer is:

5× saline sodium phosphate EDTA

5× Denhardt's solution 1 pmol/100 µl HRP-labeled HPIV-1 or HPIV-2, or HPIV-3 HN specific probe Wash 20 times with PBS at 37° C. and 8 times with PBS containing 0.05% Tween-20.

To analyze the reaction products, one would typically dilute strepavidin-HRP-conjugate 1:1000 with PBS containing 0.05% Tween-20. Add 200 ul/well and incubate at room temperature for 30 minutes. Wash 5 times with PBS containing 0.5% Tween-20. Add 200 ul/well TMB-ELISA substrate buffer (Life Technologies) in the dark. Incubate at room temperature for 15 minutes with gentle agitation. Stop with 50 ul/well 1.ON $H_2SO_4$. Incubate with gentle agitation for 5 minutes.

To interpret results, one may read optical density (OD) at 450 nM in 30 minutes. Samples with an O.D. greater than or equal to the mean of the negative control plus 3σ of the negative control are considered positive. If the O.D. is less than this, the sample is considered negative.

To quantitate the copy number of HPIV-1 RNA in the sample, plot the EHA O.D. of the standard curve and fit each sample O.D. to this plot.

Quantification Standard

The following method is useful in constructing a quantification standard: HPIV-1 virus RNA is synthesized from HPIV-1 virus genomic RNA by reverse transcription. The cDNA is amplified with a primer pair of HN1B (ACT CTG GAC TCA AGA ATG AGA AAT, SEQ ID NO:28) and HN2A (CAT ATT TGA CAA ATA GGC AGG CAT, SEQ ID NO:29) to yield a 2070 bp HN gene product. The PCR product and plasmid PCR™II (Invitrogen, San Diego, Calif.) are ligated according to the supplier's protocol. A clone is obtained and named PCR™II 2-1. This clone contains the 2070 bp HPIV-1 HN gene insert. The clone is, preferably, confirmed first by BamHI, XbaI, BamHI/XbaI digestion and then by sequencing with USB sequences PCR product sequencing kit (United States Biochemical, Cleveland). PCR™II2-1 DNA is transcribed to RNA with SP6 RNA polymerase (Promega, Madison, Wis.). The RNA is examined on denatured agarose gel, quantitated on a spectrophotometer to obtain copy number and frozen at −80° C. A known copy number of the transcript is introduced into virus genomic RNA lysis buffer and isolated with the same procedure as virus genomic RNA isolation when it is used as a quantitative standard.

Positive and negative controls which included transcript RNA from plasmid PCR™II2-1 and PCR™II are added at each assay. The cutoff value is calculated from the mean absorbance obtained from a group of seronegative samples plus three standard deviations. Copy number from subject samples are determined from the absorbances obtained from a dilution series of an RNA HN gene construct of know copy number described previously.

B. Probe Hybridization Reaction

If one chooses to use a probe hybridization reaction as an HPIV-1 assay, one must expose the probe and viral genomic RNA under conditions known in the art to allow hybridization between the probe and HPIV-1 sequence. Preferable conditions are those described in the Examples for hybridization in the EHA reaction.

The sample is then examined for the presence of the hybridization product. Preferably, this examination would comprise labeling the probe and determining whether a double-stranded labelled product is present at the end of the assay procedure.

HPIV-1, 2 and 3 Assay

If one wishes to assay for HPIV-1, 2 and 3, one could use the method of the present invention in combination with known sequences used as primers for HPIV-2 and 3. Table 5 below describes known HPIV-2 and 3 sequences. We have demonstrated that primers and probes from these known sequences are capable of amplifying and detecting HPIV-2 and 3 by RT-PCR-EHA.

HPIV-1 Assay Kit

A kit to detect HPIV-1 would contain either a selected probe or selected PCR primers labelled as described below. Additionally, substrate materials could be included, such as TMB if horseradish peroxidase is the enzyme label. A HN-specific oligonucleotide, preferably labelled, should be included.

HPIV-1, 2, and 3 RT-PCR-EHA Kit

The present invention is also a kit for the detection of HPIV-1 or, alternatively, for the detection of HPIV-1, 2 and 3. The kits are different depending on which of the three preferred PCR methods for detecting HPIV sequences one wishes to use:

PCR-EHA Method A

The kit for HPIV-1, 2 and 3 would comprise three pairs of primers for HPIV-1, HPIV-2 and HPIV-3 and three different probes specific for HPIV-1, HPIV-2 and HPIV-3. Preferable probes and primers are described in Table 5. The probes would all be enzymatically labelled. Preferable enzyme labels are also described in Table 5. Preferably, the kit would also contain substrates for enzyme detection such as TMB (3',3',5',5' tetramethylbenzidine), bromocresol purple, and PNPP (p-nitrophenylphosphate).

The procedure for using this kit would be as follows:

1. The three pairs of primers for HPIV-1, HPIV-2, and HPIV-3 are added in each of 3 tubes. A PCR reaction is then performed and PCR products are obtained.
2. The HPIV-1 probe, HPIV-2 probe and HPIV-3 probe are labeled with HRPO, alkaline phosphatase (AP) and urease, respectively.
3. One would then perform the EHA procedure described below in the Examples. One would preferably add 200 $\mu$l/well TMB-ELISA substrate for HPIV-1 detection in one well, PNPP for HPIV-3 detection in another well and bromoresol purple for HPIV-2 detection in the third well.

PCR-EHA Method B

A different kit is necessary if one wishes to use PCR-EHA method B. In this kit, one would provide three pairs of primers for HPIV-1, 2 and 3 and three HN-specific oligonucleotide probes for HPIV-1, 2 and 3. The oligonucleotides would all be attached to a protein molecule suitable for binding a solid support, such as BSA. One primer from each primer pair should be labelled enzymatically. The general procedure of PCR-EHA Method B is as follows:

1. Three pairs of primers for HPIV-1, HPIV-2, and HPIV-3 are added in each PCR tube. A PCR reaction amplifies any HPIV-1, 2 or 3 sequences.
2. BSA/HPIV-1 oligonucleotide complex, BSA/HPIV-2 oligonucleotide complex, and BSA/HPIV-3 oligonucleotide complex are coated on microtiter plates separately.
3. The products of step 1 are combined with the labelled probes and hybridization products are detected. The PCR-EHA procedure B is described above.

Alternatively, one may wish to use PCR-EHA method B with probes that are not specific for the HN protein. A suitable kit for this method would provide at least one pair of primers specific for human parainfluenza virus genome and one protein-linked oligonucleotide probe specific for the human parainfluenza virus amplification product. As above, one primer from the primer pair should be enzymatically labelled. The general procedure of PCR-EHA method B, as described above, would then be followed. Preferably, one would provide three pairs of primers and three probes specific for sequences found in human parainfluenza-1, 2 and 3 in the kit.

PCR Method C

The third PCR method is simply a PCR reaction and visualization of the PCR product. For the third PCR method, one would simply need to provide three pairs of primers for HPIV-1, 2 and 3. After the amplification reaction the PCR products would be examined on a electrophoretic gel, preferably a 2% agarose gel, and visualized. This visualization is preferably via ethidium bromide staining.

If the primers and probes described in Table 5 are used, the PCR product size for HPIV-1 is 180, for HPIV-2 is 244, and for HPIV-3 is 278 bp or 151 bp, respectively. The density of the band is examined by densitometry and compared with a standard.

We have successfully used the kit described above to assay biological samples for human parainfluenza virus-1, 2 and 3.

TABLE 5

PRIMERS AND PROBES USED IN HPIV-1, HPIV-2, HPIV-3 PCR-EHA KIT

| SUBTYPE | SEQUENCE | SIZE/PCR PRODUCT | ENZYME LABELING | SUBSTRATE |
|---|---|---|---|---|
| HPIV-1 | 5' Primer: ATT, TCT, GGA, GAT, GTC, CCG, TAG, GAG, AAC (SEQ ID NO: 19) | 180 | | |
| | 3' Primer: Biotin-CAC, ATC, CTT, GAG, TGA, TTA, AGT, TTG, ATG, A (SEQ ID NO: 20) | | | |
| | Probe: TAC, CTT, CAT, TAT, CAA, TTG, GTG, ATG, CAA, TAT, ATG (SEQ ID NO: 21) | | HRPO | TMB |
| HPIV-2 | 5' Primer: GTC, TCA TGG, ATT, CCG, ATG, ATT, CAC, AGC, AA (SEQ ID NO: 22) | 244 | | |
| | 3' Primer: GAT, GTA, CGC, TGC, ATC, ATG, CAG, AAG, CAG, A (SEQ ID NO: 23) | | | |
| | Probe: AGG, ATA, TGC, ATA, CTG, GGA, GCA, TGT, CCA, ACA, CCA (SEQ ID NO: 24) | | Urease | Bromocresal Purple |
| HPIV-3 | 5' Primer: TAT, GGA, CAA, TAA, TCC, TGG, TGT, TAT, TAT, C (SEQ ID NO: 25) | 278 | | |
| | 3' Primer: TAA, TTT, CAC, TAA, TGA, ATT, TCC, TAA, GAT, C (SEQ ID NO: 26) | | | |
| | 5' Primer: AAG, ATC, CAA, ATG, GCA, TCG, GAT, AAT, A (SEQ ID NO: 64) | 151 | | |
| | 3' Primer: TAA, TTT, CAC, TAA, TGA, ATT, TCC, TAA, GAT, C (SEQ ID NO: 65) | | | |
| | Probe: GTG, AAT, ACA, AGG, CTT, CTT, ACA, ATT, CAG, AGT, CAT (SEQ ID NO: 27) | | AP | PNPP |

Probes and Primers for Respiratory Syncytial Virus A and B and Influenza Virus A and B The present invention requires that the biological sample be examined for the presence of at least one virus selected from the group of respiratory syncytial virus A and B and influenza virus A and B. The Examples below demonstrate suitable primers and probes in Tables 7 and 8.

Preferably, primers will be selected from SEQ ID NOs:30, 31, 33, 34, 36, 37, 39, 40, 42, 43, 45, 46, 48, 49, 51, 52, 54, 55, 57 and 58. Preferably, probes will be selected from SEQ ID NOs:32, 35, 38, 41, 44, 47, 50, 53, 56 and 59.

The multiple virus assay would be performed identically to the assays described above except that multiple primers or probes will be included in the assay mix.

MISMATCHED PRIMERS AND MULTIPLE DENATURATION IMPROVE THE DETECTION OF HUMAN PARAINFLUENZA VIRUS BY QUANTITATIVE REVERSE TRANSCRIPTION-PCR-ENZYME HYBRIDIZATION ASSAY.

The final step in reverse transcription-PCR-enzyme hybridization assay (RT-PCR-EHA) is the enzymatic modification of a colourless substrate solution to a colored one. The optical density (OD) of this color change is measured on a spectrophotometer and represents the outcome of the EHA portion of the RT-PCR-EHA assay. Increasing the OD of positive samples in comparison to negative and control samples would result in increased sensitivity and specificity of the RT-PCR-EHA.

As described below in the Examples, we have developed two methods to increase the optical density of EHA. In comparison with conventional methods using matched PCR primers or conventional PCR product denaturation, the optical density is increased 3.6 times by using mismatched PCR primer concentration and 6.1 times by using multiple denaturation of the PCR products. Our data demonstrates that mismatched PCR primer concentration and multiple denaturation of the PCR products significantly increase the optical density of EHA positive samples without increasing the background. The two methods will greatly benefit the application of RT-PCR-EHA and any PCR based diagnostic test including the diagnosis of infectious diseases, cancer, genetic disease, metabolic disorders, etc.

Therefore, the present invention is also an improved method of PCR. The method comprises the step of supplying mismatched primer concentration to a PCR reaction. For example, one of the Examples below demonstrates the efficacy of mismatched primer concentrations where the 5' to 3' primer ratio is 50 μM:25 μM, 25 μM:50 μM, 12.5 μM:50 μM and 12.5 μM:25 μM. By "approximately" we mean that the ratio is within 10% of the given ratio.

The present invention is also an improved method of PCR comprising the step of denaturing the initial reaction mixture at least twice, preferably at 95° C. for 5 minutes for each denaturation. In a most preferable version of the reaction, the sample is denatured at least 4 times.

EXAMPLES

Example 1

Detection and Quantification of HPIV-1 HN Gene Amplification Products by a Nonisotopic System: RT-PCR-EHA The following describes our procedure for assaying nasal wash samples for HPIV-1:

A. Collection of nasal wash specimens.

Standard nasal washes were carried out on patients suspected of having a parainfluenza virus infection.

The specimens averaged 1–2 ml and were immediately emptied into transport tubes containing 2 ml of minimum essential medium (MEM) supplemented with 0.5% bovine serum albumin, gentamicin (5 μg/ml).

Transport tubes were kept at room temperature 0.5–3 hours in the emergency room before being refrigerated at 4° C.

The specimens were centrifuged at 2000× g for 15 minutes, and the supernatants were then divided. 0.5–1 ml aliquots were refrigerated at 4° C., until frozen at −80° C. later that day.

B. Construction of the quantitation standard.

The quantitation standard was a 2070-base RNA transcript of a plasmid designated PCR™II2-1. To construct this standard, HPIV-1 virus RNA was synthesized from HPIV-1 virus genomic RNA by reverse transcription. The cDNA was amplified with a primer pair of HN1B (ACT CTG GAC TCA AGA ATG AGA AAT, SEQ ID NO:28) and HN2A (CAT ATT TGA CAA ATA GGC AGG CAT, SEQ ID NO:29) to yield a 2070 bp HN gene product.

The PCR product and plasmid PCR™II (InVitrogen, San Diego, Calif.) were ligated under standard conditions. Transformation of INVaF'-competent cells (InVitrogen, San Diego, Calif.) with the ligated plasmid was carried out according to the suppliers protocol. A clone was obtained and named PCR™II2-1. This clone contained the 2070 bp HPIV-1 HA gene insert.

The clone was checked first by BamHI, XbaI, BamHI/XbaI digestion and then by sequencing with USB sequenase PCR product sequencing kit (United States Biochemical, Cleveland).

PCR™II2-1 DNA was transcribed to RNA with SP6 RNA polymerase (Promega, Madison, Wis.). The RNA was viewed on a denatured agarose gel, quantitated on a spectrophotometer to obtain correct copy number, and frozen at −70° C.

C. RNA Isolation Into a sterile 1.5 ml microfuge tube, 0.5 ml guanidinium solution was added to 100–200 ul tissue culture supernatant or the clinical nasal wash described above. The guanidinium solution was:

| | |
|---|---|
| Guanidinium (iso)thiocyanate | 4 M |
| Sodium Citrate, pH 7 | 25 mM |
| Sarcosyl | 2% (w/v) |
| 2-mercaptoethanol | 0.1 M |

The samples were homogenized by vortexing. 50 μl (1/10 volume) of 2M sodium acetate pH 4 was added. 500 μl (1 volume) water saturated phenol (pre-warmed) was added. 100 μl (1/5 volume) chloroform isoamyl alcohol (49:1) was added.

The mixed solution was vortexed thoroughly and then cooled on ice 5 minutes. The suspension was centrifuged in a microfuge at full speed for 15 minutes at 4° C. The RNA was present in the top aqueous phase whereas DNA and proteins were in the interphase and phenolic phases. The aqueous phase was transferred to a microfuge tube and 500 μl (1 volume) isopropanol was added. The samples were stored at −70° C. for at least 60 minutes and then spun at 4° C. for 15 minutes. RNA precipitated and formed a white-yellow pellet at the bottom of the tube. The supernatant was removed and the RNA pellet was washed twice with 70% ethanol in DEPC $H_2O$. DEPC $H_2O$ is 0.1% Diethylpyrocarbonate in water, shaken well, incubated 2 hours 37° C., and autoclaved.

The RNA pellet was vacuum dried briefly for 10–15 minutes and then dissolved by vortexing in 50 μl DEPC $H_2O$ containing 0.5 μl RNase inhibitor (Boehringer Mannheim, 50 units/ml). The RNA was stored at −20° C. or −70° C.

D. Reverse Transcription (RT) Reaction

A RT master mix was prepared:

| RT Master Mix | Volume (μl) | Final Concentration |
|---|---|---|
| 25 mM $MgCl_2$ | 4 μl | 5 mM |
| 10X PCR buffer (PEC) | 2 | 1X |
| DEPC $H_2O$ | 1 | — |
| dGTP | 2 | 1 mM |
| dATP | 2 | 1 mM |
| dTTP | 2 | 1 mM |
| dCTP | 2 | 1 mM |
| RNase inhibitor (20 units/ml) | 1 | 1 u/μl |

| RT Master Mix | Volume (μl) | Final Concentration |
|---|---|---|
| MULV reverse transcriptase | 1 | 2.5 u/μl |
| Random hexamers | 1 | 2.5 u/μl |
| | 18 μl/sample | |

18 μl RT master mix was added to a thermalcycling tube. 2 μl RNA from the sample described above was added. 2 μl quantitation standard RNA with 10, 50, 100, 1000, 5000, 10,000 copies respectively, were added and kept at room temperature for 10 minutes. The samples were incubated 42° C. for 60 minutes, then 99° C. for 5 minutes, then held at 5° C.

E. PCR Amplification

A PCR master mix was prepared:

| PCR master mix | Volume (μl) | Final Concentrations |
|---|---|---|
| 25 mM $MgCl_2$ | 2 μl | 2 mM |
| 10X PCR buffer | 4 | 1X |
| sterile distilled $H_2O$ | 31.5 | — |
| | 37.5 μl/sample | |

PCR sample tubes were prepared:

| | | |
|---|---|---|
| PCR master mix | 37.5 μl | — |
| Upstream primer PF526 | 1 | 1.0 μM |
| Downstream primer PR678 biotin | 1 | 1.0 μM |
| cDNA | 10 | — |
| Ampli Taq DNA polymerase | 0.5 | 2.5 units/50 μl |
| | 50 μl | |

The samples were overlayed with 40 μl mineral oil. The tubes were placed in a 70° C. prewarmed thermal cycler within 2 minutes of adding Ampli Taq to reduce nonspecific binding of primers and production of nonspecific products. Hot start is optional (see Ampli Taq directions).

Sequence of primer PF 526: ATT TCT GGA GAT GTC CCG TAG GAG AAC (SEQ ID NO:19).

Sequence of primer PR 678: Biotin-CAC ATC CTT GAG TGA TTA AGT TTG ATG AT (SEQ ID NO:20).

The thermalcycling program was as follows:
1. 95° C., 2 minutes (1 cycle)
2. 95° C., 1 minute; 55° C., 45 seconds; 72° C., 45 seconds, (2 cycles)
3. 94° C., 1 minute; 60° C., 45 seconds; 72° C., 45 seconds, (28 cycles)
4. 72° C., 7 minutes (final extension)

F. Denature PCR Product

To denature the DNA, the samples were incubated at 95° C. for 5 minutes and then kept on ice.

G. EHA

300 μl/well blocking solution was added to Reacti-Bind Strepavidin Coated Polystyrene Strep Plates (Pierce Catalog #15120) and incubated overnight at 4° C. The blocking solution was removed by aspiration.

Blocking solution:
5x Denhardt's solution
1% gelatin (EIA grade, BIORAD)
250 μg/ml herring sperm DNA (Promega)

70 μl/well of premixed solution was added for solution hybridization. 5 μl denatured PCR product was mixed with 65 μl hybridization buffer and incubated 42° C., 1 hour.

Hybridization buffer:

5× saline sodium phosphate EDTA

5× Denhardt's solution 1 pmol/100 μl HRP-labeled HPIV-1 HN specific probe

The sequence of HRP-labeled HPIV-1 HN specific probe was HRP-TAC, CTT, CAT, TAT, CAA, TTG, GTG, ATG, CAA, TAT, ATG (SEQ ID NO:21). The sample was washed 20 times with 1× PBS 0.05% Tween-20. 200 μl/well TMB-EHA substrate (Life Technologies Catalog #15980-014) was added, and the sample was incubated 15 minutes 20° C. in the dark. The reaction was stopped by adding 50 μl/well 1N $H_2SO_4$. The O.D. of the sample was measured at 450 nm.

H. Interpretation of results

Samples with O.D.'s greater than or equal to the mean of the negative control plus at least 3 times σ of the negative control and greater than 0.100 O.D. are considered positive. If the O.D. is less than this, it is considered negative.

To quantitate the copy number of HPIV-1 RNA in the original sample, the EHA O.D. of the standard curve was compared and the copy number with each sample was read. Table 6, below, discloses data obtained in the Example described above. Nasal samples were independently cultured and identified. Both positive and negative samples were analyzed according to the present invention.

TABLE 6

| | RT-PCR-EHA | | | |
|---|---|---|---|---|
| Specimen Group | No. Specimens | No. Positive | No. Negative | Mean of HPIV copy/mL |
| virus culture positive | 9 | 9 | 0 | 239607 |
| virus culture negative | 40 | 4 | 36 | 36528 |

The 4 positive samples from the virus culture negative samples were found to have a mean HPIV copy/ml of 36528 transcripts. The other negative samples had no copies of HPIV transcripts.

Example 2

Preparation of Primers and Probes for use in Virus Assay for Influenza A and B and Respiratory Syncytial Virus A and B Tables 7 and 8 describe primers and probes that we have successfully used in individual assays for influenza A and B virus detection and respiratory syncytial virus A and B detection by quantitative RT-PCR-EHA.

The probes and primers were prepared C-S follows:

Sequences from Genbank and published sources were examined (see Appendix 2) and appropriate probes and primers were developed (see Tables 7 and 8). Individual assays were performed as described above for HPIV with the same criteria for success. The results of the RT-PCR-EHA for RSV-A, B and influenza A and B are similar to those found for HPIV-1, 2 and 3. All primers and probes listed in Tables 7 and 8 were successful. (The numbering referred to in Tables 7 and 8 for "position of sequence" begins at the 5' end of the gene.)

TABLE 7

PRIMERS AND PROBES USED IN INFLUENZA A & B VIRUS DETECTION BY QUANTITATIVE RT-PCR EHA

| Name of Primer or Probe | Sequence | Position of Sequence | Size of PCR Product | SEQ ID NO: |
|---|---|---|---|---|
| INFAM32 | 5'Primer: CTT,CTA,ACC,GAG,GTC,GAA,ACG,TA | 32–54 | 227 | 30 |
| INFAM243 | 3'Primer: Biotin-CGT,CTA,CGC,TGC,AGT,CCT,CGC,TCA,C | 243–258 | | 31 |
| INFAM159 | Probe: HRPO-GGC,TAA,AGA,CAA,GAC,CAA,TCC,TGT,CAC,CTC,TGA,CTA,A | 159–195 | | 32 |
| INFAM75 | 5'Primer: CAG,GCC,CCC,TCA,AAG,CCG,A | 75–93 | 184 | 33 |
| INFAM243 | 3'Primer: Biotin-CGT,CTA,CGC,TGC,AGT,CCT,CGC,TCA,C | 243–258 | | 34 |
| INFAM159 | Probe: HRPO-GGC,TAA,AGA,CAA,GAC,CAA,TCC,TGT,CAC,CTC,TGA,CTA,A | 159–195 | | 35 |
| INFAM170 | 5'Primer: AGA,CCA,ATC,CTG,TCA,CCT,CTG,AC | 170–192 | 236 | 36 |
| INFAM383 | 3'Primer: Biotin-CAA,CTG,GCA,AGT,GCA,CCA,GCA,GA | 383–405 | | 37 |
| INFAM233 | Probe: HRPO-AGT,GAG,CGA,GGA,CTG,CAG,CGT,AGA,CGC,TTT,GTC,CA | 233–267 | | 38 |
| INFAM170 | 5'Primer: AGA,CCA,ATC,CTG,TCA,CCT,CTG,AC | 170–192 | 257 | 39 |
| INFAM407 | 3'Primer: Biotin-CTG,TTG,TAT,ATG,AGG,CCC,AT | 407–426 | | 40 |
| INFAM233 | Probe: HRPO-AGT,GAG,CGA,GGA,CTG,CAG,CGT,AGA,CGC,TTT,GTC,CA | 233–267 | | 41 |
| INFBNS748 | 5'Primer: ATG,GCC,ATC,GGA,TCC,TCA,ACT,CAC,TC | 748–773 | 244 | 42 |
| INFBNS967 | 3'Primer: Biotin-TCA,TGT,CAG,CTA,TTA,TGG,AGC,TGT,T | 967–991 | | 43 |
| INFBNS802 | Probe: HRPO-AGC,CAA,TTC,GAG,CAG,CTG,AAA,CTG,CGG,TGG,GAG,TC | 802–836 | | 44 |
| INFBNS748 | 5'Primer: ATG,GCC,ATC,GGA,TCC,TCA,ACT,CAC,TC | 748–773 | 244 | 45 |
| INFBNS967 | 3'Primer: Biotin-TCA,TGT,CAG,CTA,TTA,TGG,AGC,TGT,T | 967–991 | | 46 |
| INFBNS838 | Probe: HRPO-TAT,CCC,AAT,TTG,GTC,AAG,AGC,ACC,GAT,TAT,CAC,CAG | 838–873 | | 47 |

TABLE 8

PRIMERS AND PROBES USED IN RESPIRATORY SYNCYTIAL VIRUS A&B DETECTION BY QUANTITATIVE RT-PCR EHA

| Name of Primer or Probe | Sequence | Position of Sequence | Size of PCR Product | SEQ ID NO |
|---|---|---|---|---|
| RSVA1B967 | 5'Primer: ACA,ATC,TAA,AAC,AAC,AAC,TCT,ATG,C | 967–991 | 189 | 48 |
| RSVAN1136 | 3'Primer: Biotin-GTG,TAT,TTG,CTG,GAT,GAC,AG | 1136–1155 | | 49 |
| RSVA1B988 | Probe: HRPO-ATG,CAT,AAC,TAT,ACT,CCA,TAG,TCC,AGA,TGG,AGC,CTG,AA | 988–1025 | | 50 |
| RSVAF1121 | 5'Primer: ATG,AAC,AGT,TTA,ACA,TTA,CCA,AGT,GA | 1121–1146 | 182 | 51 |
| RSVAF1283 | 3'Primer: Biotin-CCA,CGA,TTT,TTA,TTG,GAT,GC | 1283–1302 | | 52 |
| RSVAF1253 | Probe: HRPO-GTG,TCA,TGC,TAT,GGC,AAA,ACT,AAA,TG | 1253–1279 | | 53 |
| RSVB1B960 | 5'Primer: AAC,TAA,CCC,ATC,CAA,ACT,AAG,CTA,TTC,CTC,AA | 960–991 | 196 | 54 |
| RSVAN1136 | 3'Primer: Biotin-GTG,TAT,TTG,CTG,GAT,GAC,AG | 1136–1155 | | 55 |
| RSVB1B989 | Probe: HRPO-CAA,ACA,ACA,GTG,CTC,AAC,AGT,TAA,GAA,GGA,GCT,AAT,CCA | 989–1027 | | 56 |
| RSVBG71 | 5'Primer: CTC,TTA,ATC,ATC,TAA,TTG,TAA,TAT,CCT | 71–97 | 149 | 57 |
| RSVBG204 | 3'Primer: Biotin-TTA,GTG,TAA,CTT,TGT,GAT,TGG,CAG,AG | 204–229 | | 58 |
| RSVBG152 | Probe: HRPO-TGG,CAA,TGA,TAA,TCT,CAA,CCT,CTC,TCA,TAA,TTG,CAG,C | 152–187 | | 59 |

Example 3

Diagnosis of Human Parainfluenza Virus Type 1, Type 2, Type 3, Respiratory Syncytial Virus A and B, and Influenza Virus A and B Infection by RT-PCR-EHA Using Mixed Primers in a Single Tube Multiplex Assay Here, we describe an RT-PCR-EHA for the detection of human parainfluenza virus type 1 (HPIV-1), type 2 (HPIV-2), type 3 (HPIV-3), respiratory syncytial virus type A (RSV-A), type B (RSV-B), influenza virus A and B RNA with mixed primers in a single tube assay. In comparison with separated RT-PCR-EHA, the single tube multiplex EHA-RT-PCR demonstrated the same sensitivity and specificity. This method will represent an important tool for the timely and sensitive diagnosis of HPIV-1, HPIV-2, HPIV-3, RSV-A, RSV-B, influenza virus A and B virus infections.

A. Materials and Methods

Virus stocks. HPIV-1 (HA-2, strain C39; American Type Culture Collection, Rockville, Md.), HPIV-2 (LRS-76 clinical isolate, 1991, Milwaukee), HPIV-3 (LRS-75 clinical isolate, 1991, Milwaukee), RSV-A (A2 strain; American Type Culture Collection), RSV-B (RSV; strain 9320; American Type Culture Collection), influenza virus A (LRS-147 clinical isolate, 1991, Milwaukee), influenza virus B (Jones strain; American Type Culture Collection) were used and prepared in our laboratory by standard protocols.

Viral genomic RNA isolation. Viral genomic RNA was extracted from frozen nasal wash specimens by previously described methods. Briefly, samples were treated with guanidinium-isothiocyanate (4 M) in sodium citrate (25 mM) buffer (pH 7.0) with 0.5% sarcoryl and 0.1 M β-mercaptoethanol; 0.1 volume of 2 M sodium acetate was added together with 1 volume of water-saturated phenol and 0.2 volume of chloroform-isoamyl alcohol (49:1. After centrifugation, RNA was extracted in the aqueous phase, and the phenol-chloroform extraction was repeated once more. The RNA was then precipitated with isopropanol at −20° C. for 1 hour. After centrifugation, the pellet was washed twice with 70% ethanol and was dissolved in 50 µl of diethyl pyrocarbonate-treated water containing 20 U of RNase inhibitor.

cDNA synthesis. cDNA was synthesized from random hexamers by incubation with murine leukemia virus (MuLV) reverse transcriptase (Perkin-Elmer Cetus, Norwalk, Conn.) and 1 mM each deoxynucleoside triphosphates at 42° C. for 60 minutes and 99° C. for 5 minutes and was soaked at 5° C. for 5 minutesFifteen nanograms each of viral RNA from virus stock was used for a single test.

Amplification of cDNA by PCR. For PCR amplification, 6½ pairs of primers (RSV A and B share a 3' primer) from highly conserved sequences of the HPIV-1, 2, and 3 HN genes, the 1B and N genes from RSV-A and B and the M gene from influenza virus A and NS gene from influenza B were used for amplification.

The primers for the HPIV-1 HN gene are HPIV-1 PF 526 (SEQ ID NO:19) and HPIV-1 PR 678 (SEQ ID NO:20); for HPIV-2 HN gene were HPIV-2 PF 301 (SEQ ID NO:22) and HPIV-2 PR 545 (SEQ ID NO:23), for HPIV-3 HN gene were HPIV-3 PF 321 (SEQ ID NO:25), and HPIV-3 PR 471 (SEQ ID NO:26).

For the RSVA IB and N gene we used RSV1B 967 (SEQ ID NO:48) and RSVAN1136 (SEQ ID NO:49), for RSVB 1B and N gene we used primers RSVB960 (SEQ ID NO:54) and RSVAN1136 (SEQ ID NO:43), for influenza virus A M gene we used primers INFAM32 (SEQ ID NO:30) and INFAM243 (SEQ ID NO:34), and for influenza virus B NS gene we used primers INFBNS748 (SEQ ID NO:45) and INFBNS967 (SEQ ID NO:46).

The assay mixture contained 10 mM Tris-HCl, 2 mM $MgCl_2$, 0.2 mM (each) deoxynucleoside triphosphates, 0.2 µM (each) primers, and 2.5 U of AmpliTaq DNA polymerase (Perkin-Elmer Cetus). After denaturation at 95° C. for 2 minutes, aliquots were then amplified by two cycles at 95° C for 1 minute, 55° C. for 45 seconds, and 72° C. for 45 seconds and 29 cycles of 95° C. for 1 minute, 60° C. for 45 seconds, and 72° C. for 45 seconds and were then held at 72° C. for 7 minutes.

The PCR products were analyzed by electrophoresis on a 2% agarose gel in TBE (Tris-borate-EDTA) buffer at 80 V for 1 hour and 15 minutes and were stained with ethidium bromide. The PCR products were also analyzed using liquid enzyme hybridization (EHA).

B. Results

The PCR products were analyzed by electrophoresis on 2% agarose gel. The seven PCR products for HPIV-1, HPIV-2, HPIV-3, RSV-A, RSV-B, influenza virus A and influenza virus B were 180 bp, 245 bp, 151 bp, 189 bp, 196 bp, 227 bp, and 244 bp. Only a specific band showed up in response to each set of primers. In comparison with RT-PCR with one pair of primers, the band obtained from RT-PCR with mixed primers in single tube reaction showed the same size and the same sensitivity. The results obtained in our experiments demonstrate the possibility for rapid diagnosis of HPIV-1, HPIV-2, HPIV-3, RSV-A, RSV-B, influenza virus A, and influenza virus B infections by RT-PCR with mixed primers in single tube reaction.

The PCR product from all seven viruses was also detected using specific probes (SEQ ID NOs:21, 24, 27, 50, 56, 32 and 47) to each virus in EHA.

Example 4

Mismatched PCR Primer Concentration Improves the Detection of HPIV-1, 2, or 3 by Quantitative RT-PCR-EHA In the Example below, we demonstrate that varying the ratio of primer concentration drastically improves PCR performance.

A. Materials and Methods

Construction of the quantitation standard. To construct a standard, HPIV-1, 2, or 3 virus cDNA was synthesized from HPIV-1, 2, or 3 virus genomic RNA by reverse transcription. The cDNA was amplified using the primer pairs (e.g., HPIV3 5'0013 (AGG, AGT AAA, GTT, ACG, CAA, T (SEQ ID NO:60)) and HPIV-3 3'1957 (TGA, TTA, CTT, ATC, ATA, TAC, TTG (SEQ ID NO:61)) to yield a 1945 bp HPIV-3 HN gene product). The PCR product and plasmid PCR™II (Invitrogen, San Diego, Calif.) were ligated under standard conditions. Transformation of INVaF'-competent cells (Invitrogen, San Diego, Calif.) with the ligated plasmid was carried out according to the supplier's protocol. PCR™II HPIV-1, 2 or 3 HN DNA was transcribed to RNA with SP6 RNA polymerase (Promega, Madison, Wis.). The RNA was examined on a denatured Agarose gel, quantitated on a spectrophotometer to obtain the copy number and frozen at −70° C.

cDNA synthesis. cDNA was synthesized from random hexamers by incubation at 42° C. for 60 minutes, 99° C. for 5 minutes, and soaked at 5° C. for 5 minutes w-th MuLV reverse transcriptase (Perkin-Elmer Cetus, Norwalk, Conn.) and 1 mM dNTP. Fifteen nanograms of virus RNA from virus stocks was used for a single test.

Amplification of cDNA by PCR. For PCR amplification, primers from highly conserved sequences of the HPIV-1, 2, or 3 HN gene (e.g., PF 321-AAG, ATC, CAA, ATG, GCA, TCG, GAT, AAT, A, SEQ ID NO:62, from bp 321 to 345 sense), and PR 471-TAA, TTT, CAC, TAA, TGA, ATT, TCC, TAA, GAT, C, SEQ ID NO:63, from bp 443 to 471, antisense) were used for amplification. HPIV-1, 2, or 3 primers (e.g., PR 471) were biotinylated at the 5' end (Operon, Alameda, Calif.). To optimize the PCR primer concentration, 11 pairs of different primer concentrations were tested in RT-PCR-EHA using HPIV-1, 2, or 3 specific primer pairs (Table 9). The PCR mixture contained 10 mM Tris, 2 mM MgCl, 0.2 mM dNTP, and 2.5 U Ampli Taq DNA polymerase (Perkin-Elmer Cetus, Norwalk, Conn.). After denaturation at 95° C. 2 minutes, aliquots were then amplified by two cycles of 95° C. for 1 minute, 55° C. for 45 seconds, 72° C. for 45 seconds, 34 cycles at 95° C. for 1 minute, 60° C. for 45 seconds, 72° C. for 45 seconds, and hold at 72° C. for 7 minutes. After final extension at 72° C. for 7 minutes, PCR products were denatured by heating at 95° C. for 5 minutes and then kept on ice (standard conditions). To optimize the effect of heat denaturation on the RT-PCR-EHA, PCR products were denatured by using different heating conditions and then kept on ice (Table 10). Positive and negative controls which included transcript RNA from plasmid PCR™ HPIV-1, 2, or 3 HN and PCR™II were added to each assay.

The PCR products were analyzed by electrophoresis on 2% agarose gel in TBE buffer, 80 volts for 1 hour 15 minutes, and stained with ethidium bromide.

Detection and quantitation of PCR product by enzyme-hybridization assay (EHA). To detect and quantitate the PCR products, 96-well microplates were coated with streptavidin. Wells were then filled with 300 µl of a blocking solution containing 5× Denhardt's solution, 1% gelatin, 250 µg/ml sheared herring sperm DNA (Promega, Madison, Wis.) at 4° C. Immediately before use, the blocking solution was aspirated from each well and 5 µl of the previously made PCR products and 65 µl of a hybridization solution containing 5× saline sodium phosphate EDTA, 5× Denhardt's solution, and 1 pmol/100 µl of HRP-labeled HPIV 1, 2, or 3 specific probe (e.g., HPIV-3 HN probe 369-GTG, AAT, ACA, AGG, CTT, CTT, ACA, ATT, CAG, AGT, CAT, SEQ ID NO:27, from 369 to 401, sense) were added to individual wells. A capture and hybridization reaction was then carried out in the well for 1 hour at 42° C. The 96-well microplate was washed with PBS containing 0.05% Tween-20. 200 µl of substrate solution TMB-ELISA, (Life Technologies), was added to each well. After 15 minutes the reaction was stopped with 1 N $H_2SO_4$ and the optical density of each well was measured at 450 nm on a spectrophotometer (Biotek, EL3).

Results and Discussion

Table 9 tabulates the results of varying primer concentration:

TABLE 9

OPTIMIZATION OF PCR PRIMER CONCENTRATION IN RT-PCR-EHA

| PCR Primer | 1 | 2 | 3 | 4 | 5 | 6 | 7 | 8 | 9 | 10 | 11 |
|---|---|---|---|---|---|---|---|---|---|---|---|
| PF321, 5' Primer† | 50* | 25 | 12.5 | 6.25 | 50 | 50 | 50 | 25 | 12.5 | 6.25 | 12.5 |
| PR471, 3' Primer† Biotinylated | 50 | 25 | 12.5 | 6.25 | 25 | 12.5 | 6.25 | 50 | 50 | 50 | 25 |
| Optical Density† | 0.200 | 0.257 | 0.026 | 0.021 | 0.455 | 0.047 | 0.012 | 0.380 | 0.652 | 0.244 | 0.717 |

*Primer concentration in µM.
‡Measured specific primers at 450 nanometers (A450).
†HPIV-3 specific primers.

In comparison with conventional matched PCR primers (50 µM each), mismatched PCR primer concentration (5' primer PF 321 at concentration 12.5 µM, and biotinylated 3' primer PR471, at concentration 25 µM) showed a 3.59 times increase in optical density. Mismatched primer concentration may create more biotin-labeled PCR product which will be captured by the streptavidin coated plate and thereby increase the value of optical density reading.

TABLE 10

MULTIPLE DENATURATION OF THE PCR PRODUCT IMPROVES THE DETECTION OF HPIV-1, 2, OR 3 BY QUANTITATIVE RT-PCR-EHA.

| DENATURE CONDITION | 1 | 2 | 3 | 4 | 5 | 6 | 7 |
|---|---|---|---|---|---|---|---|
| Denature Temperature (° C.) and time (min) | 95° C., 5' | 95° C., 10' | 95° C., 15' | 95° C., 20' | 95° C., 5' | 95° C., 5' | 95° C., 5' |
| Time Kept on ice (min) | 10' | 10' | 10' | 10' | 10' | 10' | 10' |
| Time(s) | x1 | x1 | x1 | x1 | x2 | x3 | x4 |
| Value of optical density | 0.185 | 0.145 | 0.162 | 0.182 | 0.561 | 0.584 | 1.126 |

In comparison with the conventional heat denaturation method (#1, Table 10) the optical density using the double denaturation method (#5, Table 10) increased 3.03 times and the four time denaturation method (#7, Table 10) showed a 6.05 times higher OD. However, lengthening the denaturation time did not increase the optical density. Multiply denatured PCR product demonstrated more single-stranded DNA on agarose gel. This would allow more binding of viral-specific probes (also single-stranded) during the EHA portion of the RT-PCR-EHA. Increased probe binding would then lead directly to increased OD in the test well.

We claim:

1. A method of detecting multiple virus infection in a biological sample comprising the steps of (a) isolating nucleic acid from a biological sample, (b) exposing the nucleic acid or cDNA created from the nucleic acid to primer pairs specific for human parainfluenza virus-1, 2 and 3, respiratory syncytial virus A and B and influenza virus A and B sequences under conditions suitable for nucleic acid amplification, wherein the primers selectively amplify the virus sequence and not other sequences, wherein an amplification product is formed if the sample contains any of the viruses and wherein the amplification comprises the improvement of supplying 5' and 3' primers of unequal concentrations wherein the product is double-stranded PCR products, and (c) determining whether the amplification product is present by exposing the step (b) products to protein-linked oligonucleotide probes, wherein the protein is capable of binding to a solid support, under conditions suitable for hybridization between complementary nucleic acid sequences, binding the oligonucleotide to the solid support, and examining the probes for the presence of a hybridization product, wherein the oligonucleotide probes are of a sequence identical to a viral sequence.

* * * * *

UNITED STATES PATENT AND TRADEMARK OFFICE
CERTIFICATE OF CORRECTION

Patent No. : 6,015,664
Dated : Jan. 18, 2000
Inventor : Kelly J. Henrickson et al.

It is certified that error appears in the above-identified patent and that said Letters Patent is hereby corrected as shown below:

In the Abstract:
Line 7, after the second occurrence of "virus", please delete ",".

Column 1, line 33, please delete "T." and substitute --J.--.

Column 2, line 23, please delete "parainfluenaza" and substitute --parainfluenza--.

Column 4, line 12, please delete "-he" and substitute --the--.

Column 6, line 1, after "chosen" please delete -- - --.

Patent No. : 6,015,664   Page 2 of 2
Dated : Jan. 18, 2000
Inventor : Kelly J. Henrickson et al.

Column 8, line 14, please delete "3" and substitute --3'--.
    Column 10, line 12, please delete "dejected" and substitute --detected--.

Column 20, line 25, please delete "C-S" and substitute --as--.
    Column 21, line 55, after "1" please insert --)--.
    Column 23, line 37, please delete "w-th" and substitute --with--.

Signed and Sealed this

Eighth Day of May, 2001

*Attest:*

NICHOLAS P. GODICI

*Attesting Officer*     Acting Director of the United States Patent and Trademark Office